(12) United States Patent
Huber et al.

(10) Patent No.: US 8,710,019 B2
(45) Date of Patent: Apr. 29, 2014

(54) TOPICAL ANTIBIOTIC COMPOSITION FOR THE PREVENTION OF LYME DISEASE

(75) Inventors: Gustave Huber, Zürich (CH); Uta Hüttenes, Zürich (CH); Caroline Roosens-von Bidder, Zürich (CH)

(73) Assignee: Ixodes AG, Zürich (CH)

( * ) Notice: Subject to any disclaimer, the term of this patent is extended or adjusted under 35 U.S.C. 154(b) by 79 days.

(21) Appl. No.: 12/452,805

(22) PCT Filed: Jul. 24, 2008

(86) PCT No.: PCT/EP2008/059696
§ 371 (c)(1),
(2), (4) Date: Jan. 22, 2010

(87) PCT Pub. No.: WO2009/013331
PCT Pub. Date: Jan. 29, 2009

(65) Prior Publication Data
US 2010/0130437 A1    May 27, 2010

(30) Foreign Application Priority Data
Jul. 25, 2007    (EP) .................................. 07113143

(51) Int. Cl.
*A61K 31/70*    (2006.01)

(52) U.S. Cl.
USPC ............................................................ 514/29

(58) Field of Classification Search
USPC ............................................................ 514/29
See application file for complete search history.

(56) References Cited

U.S. PATENT DOCUMENTS 6,239,113 B1 *    5/2001    Dawson et al. .................. 514/29
2005/0276842 A1 *    12/2005    Zhang et al. .................. 424/448

OTHER PUBLICATIONS

Shin et al, "Topical Prophylaxis for Lyme Disease after Tick Bite in a Rodent Model", Journal of Infectious Diseases, vol. 168, No. 4, 1993, pp. 1042-1045.*

Massarotti et al, "Treatment of early Lyme disease", American Journal of Medicine, vol. 92 (4), Apr. 1992, pp. 396-403.*

* cited by examiner

*Primary Examiner* — Elli Peselev
(74) *Attorney, Agent, or Firm* — Wenderoth, Lind & Ponack, L.L.P.

(57) ABSTRACT

The invention relates to topical pharmaceutical compositions and methods related to *Borrelia burgdorferi* toxins, in particular, the present invention provides compositions and methods for the treatment of infections caused by *Borrelia burgdorferi* and in particular for the prevention of Lyme disease.

1 Claim, No Drawings

TOPICAL ANTIBIOTIC COMPOSITION FOR THE PREVENTION OF LYME DISEASE

FIELD OF THE INVENTION

The invention relates to topical pharmaceutical compositions and methods related to *Borrelia burgdorferi* toxins, in particular, the present invention provides compositions and methods for the treatment of infections caused by *Borrelia burgdorferi* and in particular for the prevention of Lyme disease.

BACKGROUND OF THE INVENTION

Lyme disease is a potentially severe and complex multi-system disorder associated with the tick-borne *Borrelia burgdorferi* toxins. The disease is transmitted to humans and other animals through arthropod bites. The *Borrelia* species are maintained in nature by cycling through the wild animals (e.g., deer, rodents and fowl) and the ticks that feed upon them. Lyme disease was first officially recognized in North America in 1975, and has become recognized as the most prevalent tick-borne disease in the U.S. This recognition was due to an outbreak of disease in children in Lyme, Conn. The disease is now recognized as having a worldwide distribution.

In the northeastern United States, Wisconsin and Minnesota, the deer tick, *Ixodes dammini* is the primary vector, while in the western United States and Europe, *I. pacifious* and *I. ricinus* are the main vectors, respectively.

The clinical symptoms of Lyme disease vary among individuals and during the time course of infection, and range from a relatively benign skin rash to severe arthritic, neurologic and cardiac manifestations. The most common clinical manifestation is the distinctive skin rash ("erythema migrans," "erythema chronicam migrans," or "ECM") which follows the bite of an infected tick. This rash is often accompanied by headache, stiff neck, myalgias, arthralgias, malaise, fatigue, and/or lymph node swelling. Weeks to months later, some infected patients develop meningoencephalitis, myocarditis, or migrating musculoskeletal pain. Even later in the course of disease, patients may experience intermittent attacks of oligoarticular arthritis or chronic arthritis in large joints, particularly in the knee. Other clinical syndromes are reported that may have the same etiologic agent include lymphocytoma (lymphadenosis benigna cutis), acro-dermalitis chronica atrophicans, tick-borne meningoradiculitis (Garin-Bujadoux-Bannwarth's syndrome), and myositis. Due to increased awareness and reporting, reported cases of Lyme disease have increased over time. Between 1982 and 1992, approximately 50,000 cases of Lyme disease were reported to the Centers for Disease Control (CDC), with 48 states reporting cases by 1992.

When the risk of Lyme disease is great, oral antibiotics are frequently administered to people who have been bitten by ticks. However, liberal oral administration of antibiotics is controversial and the risk of infection has to be balanced against indiscriminate long-term treatment with antibiotics. As an alternative, the topical application of certain antibiotics (Chien-Ming Shih and Andrew Spielman, "Topical Prophylaxis for Lyme Disease after Tick Bite in a Rodent Model", The Journal of Infectious Diseases, 1993, 168, p. 1042-1045) was evaluated and it could be shown that in a rodent model local infection was not detectable after such treatment. These studies further demonstrated, that by means of Xenodiagnosis, no *B. burgdorferi* were detected 28 days after the tick feeding. These findings, however, make no conclusive statement whether the transfer of *B. burgdorferi* from the site of infection to *Borrelia*'s target organs can be effectively be prevented.

*B. burgdorferi* is presenting several morphological forms with different sensitivity to antibiotics and environmental stress, such as exposure to distilled water or freeze-thaw cycles. Cystic forms (also called spheroplasts or starvation forms) have the ability to reconvert into normal motile spirochetes both in vitro and in vivo [Brorson O. et al., Infection. 1997 July-August; 25(4):240-6]. The presence of various atypical spirochete forms: spheroplastic L (without cell walls), cystic, and granular "blebs" has also been reported. One may therefore distinguish spirochetal forms, which are linked with high metabolic and proliferative activity, from cystic and spherical forms, which are dormant with minimal biochemical activity.

In view of debilitating nature of the advanced stages of the disease, compositions and methods for disease prevention remain critical. However, these needs have not previously been satisfactorily met.

DETAILED DESCRIPTION OF THE INVENTION

It has now surprisingly been found that a topical application of an antibiotic administered to the site of a tick bite prevents an infection by the Lyme disease. In order to prevent the infection of Lyme disease, it is essential that the *Borrelia burgdorferi* bacterium is eradicated in the early stages of infection when the prevailing form is the spirochetal form. A rapid, sustained, and extensive penetration into intracellular and interstitial tissue compartments has therefore to be achieved as well as antibiotics used showing prolonged tissue and serum half-lives. Achieving high tissue concentration was also found necessary to eradicate all forms of *Borrelia burgdorferi* including those presenting in cystic or spherical forms which would otherwise serve as a reservoir for a new outbreak of Lyme disease.

The studies underlying the present invention demonstrate, that the new composition presented here with an antibiotic effectively removes *B. burgdorferi* at the site of tick-feed and, furthermore and unexpectedly, from tissues/organs in which *B. burgdorferi* persist. This finding is particularly important, as it has been found that *B. burgdorferi* preferentially persist in these tissues/organs, rather than the circulation only. These findings are particularly important for target tissues of *Borrelia*, such as heart, bladder, joints and ear. Only if eradication of *B. burgdorferi* from these tissues can be demonstrated, the success of a treatment including a topical treatment administered to the site of tick-feed can be guaranteed.

In the context of the present invention "*Borrelia burgdorferi*" encompasses the genospecies complex *Borrelia burgdorferi* sensu lato, particular examples being *Borrelia afzelii*, *Borrelia garinii*, *Borrelia burgdorferi* sensu stricto, *Borrelia valaisiana*, *Borrelia spielmanii*, *Borrelia lusitaniae*, *Borrelia babesiosis* and *Borrelia erlichiosis*. The present invention in particular relates to *Borrelia burgdorferi* sensu stricto.

In the context of the present invention "Lyme disease" encompasses Lyme disease and related diseases such as, for example, Southern Tick Associated Rash Illness (STARI) and Rocky Mountains spotted fever. The present invention in particular relates to Lyme disease specifically.

A first aspect of the invention is the use of an antibiotic for the preparation of a topical pharmaceutical composition for the prevention of Lyme disease.

A further aspect of the invention is the use of an antibiotic for the preparation of a topical pharmaceutical composition for the elimination of *Borrelia burgdorferi* resulting from a tick bite.

A further aspect of the invention is the use of an antibiotic for the preparation of a topical pharmaceutical composition for the elimination of spirochetal forms of *Borrelia burgdorferi* resulting from a tick bite.

A further aspect of the invention is the use of an antibiotic for the preparation of a topical pharmaceutical composition for the elimination of cystic and spherical forms of *Borrelia burgdorferi* resulting from a tick bite.

A further aspect of the invention is the method for preventing Lyme disease comprising administering a therapeutically effective amount of an antibiotic in the form of a topical pharmaceutical composition to the site of the tick bite to a patient in need thereof.

A further aspect of the present invention is related to a topical pharmaceutical composition, in particular for the prevention of Lyme disease or for the elimination of *Borrelia burgdorferi* (including spirochetal, cystic and/or spherical forms) resulting from a tick bite comprising an antibiotic, a volatile solvent (defined as water or a solvent more volatile than water) and, optionally, a solidifying agent.

The different aspects of the invention are described now in more detail whereby the given examples and preferences apply to all of the above aspects unless otherwise stated.

For example, a suitable antibiotic is selected from rifamycin, penicillin G, penicillin V, methicillin, oxacillin, cloxacillin, dicloxacillin, nafcillin, ampicillin, amoxicillin, carbenicillin, ticarcillin, mezlocillin, piperacillin, azlocillin, temocillin, cepalothin, cephapirin, cephradine, cephaloridine, cefazolin, cefamandole, cefuroxime, cephalexin, cefprozil, cefaclor, loracarbef, cefoxitin, cefmatozole, cefotaxime, ceftizoxime, ceftriaxone, cefoperazone, ceftazidime, cefixime, cefpodoxime, ceftibuten, cefdinir, cefpirome, cefepime, BAL5788, BAL9141, imipenem, ertapenem, meropenem, astreonam, clavulanate, sulbactam, tazobactam, streptomycin, neomycin, kanamycin, paromycin, gentamicin, tobramycin, amikacin, netilmicin, spectinomycin, sisomicin, dibekalin, isepamicin, tetracycline, chlortetracycline, demeclocycline, minocycline, oxytetracycline, methacycline, doxycycline, erythromycin, azithromycin, clarithromycin, dirithromycin, roxithromycin, telithromycin, troleandomycin, ABT-773, lincomycin, clindamycin, vancomycin, oritavancin, dalbavancin, teicoplanin, quinupristin and dalfopristin, sulphanilamide, paraaminobenzoic acid, sulfadiazine, sulfisoxazole, sulfamethoxazole, sulfathalidine, linezolid, nalidixic acid, oxolinic acid, norfloxacin, perfloxacin, enoxacin, ofloxacin, ciprofloxacin, temafloxacin, lomefloxacin, fleroxacin, grepafloxacin, sparfloxacin, trovafloxacin, clinafloxacin, gatifloxacin, moxifloxacin, gemifloxacin, sitafloxacin, metronidazole, daptomycin, garenoxacin, ramoplanin, faropenem, polymyxin, tigecycline, AZD2563, and trimethoprim. Preferably, the antibiotic is selected from azithromycin, clarithromycin, dirithromycin, roxithromycin, telithromycin, troleandomycin, chlortetracycline, demeclocycline, minocycline, oxytetracycline and methacycline. Also preferred are antibiotics selected from the classes of macrolides and tetracyclines. Most preferably, the antibiotic is azithromycin. In a further embodiment more than one antibiotic, for example two antibiotics, may be present in the composition.

For most compositions, the weight percentage of the antibiotic can be from about 1 wt % to about 30 wt %, preferably from about 3 wt % to about 20 wt % and more preferably from about 7 wt % to about 20 wt %, based on the total weight of the composition. The weight percentage of the antibiotic is preferably at least 1 wt %, more preferably at least 3 wt %, even more preferably at least 5 wt % and most preferably at least 7 wt % based on the total weight of the composition. The weight percentage of the antibiotic is preferably at most 30 wt %, more preferably at most 20 wt % and most preferably at most 15 wt % based on the total weight of the composition. Given the minimum and maximum amounts above, the weight percentage of the antibiotic is, for example, from 1 wt % to 20 wt % or from 3 wt % to 15 wt % based on the total weight of the composition.

"Topical pharmaceutical composition" shall mean a pharmaceutical composition delivering a therapeutically effective amount of the antibiotic to a skin tissue, and subsequent absorption into the skin that may occur. Examples of such topical pharmaceutical compositions are liquids, lacquers, creams, pastes, gels, sprays, ointments, patches and varnishes. In addition to said topical compositions in a strict sense, in connection with the instant invention, a topical pharmaceutical composition also relates to compositions useful for subcutaneous injection, application by scratching the skin (as for example known from pox vaccines), treatment in presence of an occlusive environment, e.g. as a result of a patch, a dressing or any chemical treatment preceding or succeeding or during the application of the therapeutic with the aim to enhance the topical delivery.

"Therapeutically effective amount" or the like, as it relates to a drug, refers to sufficient amounts or delivery rates of a drug which achieves any appreciable level of therapeutic results in treating a condition for which the drug is being delivered. It is understood that "appreciable level of therapeutic results" may or may not meet any government agencies' efficacy standards for approving the commercialization of a product. It is understood that various biological factors may affect the ability of a substance to perform its intended task. Therefore, a "therapeutically effective amount" may be dependent in some instances on such biological factors to some degree. However, for each drug, there is usually a consensus among those skilled in the art on the range of doses that are sufficient in most subjects. Further, while the achievement of therapeutic effects may be measured by a physician or other qualified medical personnel using evaluations known in the art, it is recognized that individual variation and response to treatments may make the achievement of therapeutic effects a subjective decision. The determination of a therapeutically effective amount or delivery rate is well within the ordinary skill in the art of pharmaceutical sciences and medicine.

Before application to the skin, the topical pharmaceutical composition is in its initial, less-than-solid form, such as lacquer, liquid, cream, gel, paste or ointment. After applying a layer of such a composition on the skin area to be treated, the evaporation of the volatile solvent(s), with the help from the solidifying agent, can convert the composition layer into a soft, flexible, coherent solid layer that is optionally peelable. The soft, flexible, coherent solid layer is designed to adhere to the skin for a substantial duration, preferably longer than 30 minutes.

The application viscosity of the topical pharmaceutical composition is typically more viscous than a water-like liquid, but less viscous than a soft solid. Examples of preferred viscosities include materials that have consistencies similar to pastes, gels, ointments, and the like, e.g., viscous liquids that flow but are not subject to spilling. This means the composition has a viscosity that is high enough so that the composition does not substantially run off the skin after being applied to skin, but also has a low enough viscosity so that it can be easily spread onto the skin.

In some embodiments of the present invention, it may be desirable to add an additional agent or substance to the topical pharmaceutical composition so as to provide enhanced or increased adhesive characteristics. The additional adhesive agent or substance can be an additional solidifying agent or a non-volatile solvent (defined as less volatile than water). The non-volatile solvent stays in the formulation for substantially the entire duration of the application and serves as vehicle solvent for delivering the drug into the skin (a fraction of the non-volatile solvent(s) may be absorbed by skin during the application). Non-limiting examples of substances which might be used as additional adhesion enhancing agents include copolymers of methylvinyl ether and maleic anhydride (Gantrez polymers), polyethylene glycol and polyvinyl pyrrolidone, gelatin, low molecular weight polyisobutylene rubber and/or various aliphatic resins and aromatic resins.

In selecting the various components that can be used, e.g., antibiotic, volatile solvent(s) and solidifying agent(s), etc., many variations can be considered.

For example, the volatile solvent may be one or more volatile solvents (at least as volatile as water, including water). In one embodiment of the present invention, the volatile solvent can include a member of ethanol, isopropyl alcohol, propanol, dimethylsulfoxid, dimethyl ether, diethyl ether, butane, propane, isobutene, ethyl acetate, acetone, water, or combinations thereof. In another embodiment of the present invention, the volatile solvent can include iso-amyl acetate, denatured alcohol, methanol, propanol, isopropylalcohol, isobutene, pentane, hexane, chlorobutanol, turpentine, cytopentasiloxane, cyclomethicone, methyl ethyl ketone, or combinations thereof. The volatile solvent can include a mixture or combination of any of the volatile solvents set forth in the embodiments above. A preferred volatile solvent is ethanol, water or a combination thereof.

The volatile solvents should be chosen to be compatible with the rest of the formulation. It is desirable to use an appropriate weight percentage of the volatile solvent(s) in the formulation. Too much of the volatile solvent system prolongs the drying time. Too little of the volatile solvent system can make it difficult to spread the composition on the skin. For most compositions, the weight percentage of the volatile solvent(s) can be from about 40 wt % to about 99 wt %, preferably from about 40 wt % to about 95 wt % and more preferably from about 50 wt % to about 95 wt %, based on the total weight of the composition. In case of a composition comprising only antibiotic and volatile solvent, the weight percentage of the volatile solvent(s) is at least 70 wt % based on the total weight of the composition.

Non-volatile solvent(s) that can be used alone or in combination to form non-volatile solvent systems can be selected from a variety of pharmaceutically acceptable liquids. In one embodiment of the present invention, the non-volatile solvent system can include glycerol, propylene glycol, isostearic acid, oleic acid, propylene glycol, trolamine, tromethamine, triacetin, sorbitan monolaurate, sorbitan monooleate, sorbitan monopalmitate, butanol, or combinations thereof. In another embodiment the non-volatile solvent system can include benzoic acid, butyl alcohol, dibutyl sebacate, diglycerides, dipropylene glycol, eugenol, fatty acids such as coconut oil, fish oil, palm oil, grape seed oil, isopropyl myristate, mineral oil, oleyl alcohol, vitamin E, triglycerides, sorbitan fatty acid surfactants, triethyl citrate, or combinations thereof. In a further embodiment, the non-volatile solvent system can include 1,2,6-hexanetriol, alkyltriols, alkyldiols, acetyl monoglycerides, tocopherol, alkyl dioxolanes, p-propenylanisole, anise oil, apricot oil, dimethyl isosorbide, alkyl glucoside, benzyl alcohol, bees wax, benzyl benzoate, butylene glycol, caprylic/capric triglyceride, caramel, cassia oil, castor oil, cinnamaldehyde, cinnamon oil, clove oil, coconut oil, cocoa butter, coco-glycerides, coriander oil, corn oil, coriander oil, corn syrup, cottonseed oil, cresol, cyclomethicone, diacetin, diacetylated monoglycerides, diethanolamine, diethylene glycol monoethyl ether, diglycerides, ethylene glycol, eucalyptus oil, fat, fatty alcohols, flavors, liquid sugars ginger extract, glycerin, high fructose corn syrup, hydrogenated castor oil, IP palmitate, lemon oil, lime oil, limonene, milk, monoacetin, monoglycerides, nutmeg oil, octyldodecanol, olive alcohol, orange oil, palm oil, peanut oil, PEG vegetable oil, peppermint oil, petrolatum, phenol, pine needle oil, polypropylene glycol, sesame oil, spearmint oil, soybean oil, vegetable oil, vegetable shortening, vinyl acetate, wax, 2-(2-(octadecyloxy)ethoxy)ethanol, benzyl benzoate, butylated hydroxyanisole, candelilla wax, carnauba wax, ceteareth-20, cetyl alcohol, polyglyceryl, dipolyhydroxy stearate, PEG-7 hydrogenated castor oil, diethyl phthalate, diethyl sebacate, dimethicone, dimethyl phthalate, PEG Fatty acid esters such as PEG-stearate, PEG-oleate, PEG-laurate, PEG fatty acid diesters such as PEG-dioleate, PEG-distearate, PEG-castor oil, glyceryl behenate, PEG glycerol fatty acid esters such as PEG glyceryl laurate, PEG glyceryl stearate, PEG glyceryl oleate, hexylene glycerol, lanolin, lauric diethanolamide, lauryl lactate, lauryl sulfate, medronic acid, methacrylic acid, multisterol extract, myristyl alcohol, neutral oil, PEG-octyl phenyl ether, PEG-alkyl ethers such as PEG-cetyl ether, PEG-stearyl ether, PEG-sorbitan fatty acid esters such as PEG-sorbitan diisosterate, PEG-sorbitan monostearate, propylene glycol fatty acid esters such as propylene glycol stearate, propylene glycol, caprylate/caprate, sodium pyrrolidone carboxylate, sorbitol, squalene, stear-o-wet, triglycerides, alkyl aryl polyether alcohols, polyoxyethylene derivatives of sorbitan-ethers, saturated polyglycolyzed C8-C10 glycerides, N-methylpyrrolidone, honey, polyoxyethylated glycerides, dimethyl sulfoxide, azone and related compounds, dimethylformamide, N-methyl formamide, fatty acid esters, triglyceride oils, such as containing plant derived carylic/capric triglycerides (Miglyol 812), fatty alcohol ethers, alkyl-amides (N,N-dimethylalkylamides), N-methylpyrrolidone related compounds, ethyl oleate, polyglycerized fatty acids, glycerol monooleate, glycerol triacetate, glyceryl monomyristate, glycerol esters of fatty acids, silk amino acids, PPG-3 benzyl ether myristate, Di-PPG2 myreth 10-adipate, honeyquat, sodium pyroglutamic acid, abyssinica oil, dimethicone, macadamia nut oil, limnanthes alba seed oil, cetearyl alcohol, PEG-50 shea butter, shea butter, aloe vera juice, phenyl trimethicone, hydrolyzed wheat protein, or combinations thereof. In yet a further embodiment the non-volatile solvent system can include a combination or mixture of non-volatile solvents set forth above. One further benefit of the mixing of the non-volatile solvents is that it may optimize the pH of the formulation or the skin tissues under the formulation layer to minimize irritation. Preferred non-volatile solvents are selected from isopropyl myristate and saturated polyglycolyzed C8-C10 glycerides or combinations thereof. Preferred compositions according to the instant invention do not contain glycerol monooleate.

For most compositions, the weight percentage of the non-volatile solvent(s) can be from about 2 wt % to about 30 wt %, and more preferably from about 2 wt % to about 20 wt %, based on the total weight of the composition.

The selection of the solidifying agent can also be carried out in consideration of the other components present in the topical pharmaceutical composition. An appropriate solidifying agent is compatible with the composition such that the composition is in liquid or semi-liquid state, e.g. cream, paste, gel, ointment, etc., before any evaporation of the volatile solvent(s) and becomes a soft, coherent solid after the evaporation of at least some of the volatile solvent(s). The solidifying agent can be selected or formulated to be compatible with the antibiotic and the solvent vehicle (including the volatile solvent(s) and the non-volatile solvent(s), as the case may be), as well as provide desired physical properties to the solidified layer once it is formed. Depending on the antibiotic, solvent vehicle, and/or other components that may be present, the solidifying agent can be selected from a variety of agents. In one embodiment, the solidifying agent can include polyvinyl alcohol with a MW range of 20,000-70,000 (Amresco), esters of polyvinylmethylether/maleic anhydride copolymer (ISP Gantrez ES-425 and Gantrez ES-225) with a MW range of 80,000-160,000, neutral copolymer of butyl methacrylate and methyl methacrylate (degussa Plastoid B) with a MW range of 120,000-180,000, dimethylaminoethyl methacrylate-butyl methacrylate-methyl methacrylate copolymer (degussa Eudragit E100) with a MW range of 100,000-200,000, ethyl acrylate-methyl methacrylate-trimethylammonioethyl methacrylate chloride copolymer with a MW greater than 5,000 or similar MW to Eudragit RLPO (Degussa), Zein (prolamine) with a MW greater than 5,000 (Zein, MW around 35,000, Freeman industries), pregelatinized starch having a MW similar to Instant Pure-Cote B793 (Grain Processing Corporation), ethyl cellulose with a MW greater than 5,000 or a MW similar to Aqualon EC N7, N10, N14, N22, N50, or N100 (Hercules), fish gelatin having a MW range of 20,000-250,000 (Norland Products), gelatin, other animal sources with a MW range greater than 5,000, acrylates/octyl-acrylamide copolymer with a MW range greater than 5,000 or a MW similar to National Starch and Chemical Dermacryl 79.

In another embodiment, the solidifying agent can include ethyl cellulose, hydroxy ethyl cellulose, hydroxy methyl cellulose, hydroxy propyl cellulose, hydroxypropyl methyl cellulose, carboxymethyl cellulose, methyl cellulose, polyether amides, corn starch, pregelatinized corn starch, polyether amides, shellac, polyvinyl pyrrolidone, polyisobutylene rubber, polyvinyl acetate phthalate, or combinations thereof. In a further embodiment, the solidifying agent can include ammonia methacrylate, carrageenan, cellulose acetate phthalate aqueous such as CAPNF from Eastman, carboxy polymethylene, cellulose acetate (microcrystalline), cellulose polymers, divinyl benzene styrene, ethylene vinyl acetate, silicone, guar gum, guar rosin, gluten, casein, calcium caseinate, ammonium caseinate, sodium caseinate, potassium caseinate, methyl acrylate, microcrystalline wax, polyvinyl acetate, PVP ethyl cellulose, acrylate, PEG/PVP, xantham gum, trimethyl siloxysilicate, maleic acid/anhydride colymers, polacrilin, poloxamer, polyethylene oxide, poly glactic acid/poly-l-lactic acid, turpene resin, locust bean gum, acrylic copolymers, polyurethane dispersions, dextrin, polyvinyl alcohol-polyethylene glycol co-polymers, methyacrylic acid-ethyl acrylate copolymers such as BASF's Kollicoat polymers, methacrylic acid and methacrylate based polymers such as poly(methacrylic acid), or combinations thereof. In yet a further embodiment, the solidifying agent can include a combination of solidifying agents set forth in the any of the above discussed embodiments. Other polymers may also be suitable as the solidifying agent, depending on the solvent vehicle components, the drug, and the specific functional requirements of the given formulation.

In one embodiment of the present invention, the solidifying agent includes a methacrylic polymer or copolymer such as methyacrylic acid-ethyl acrylate copolymer, butyl and methyl methacrylate copolymer, aminoalkyl methacrylate copolymer, and/or an ammonioalkyl methacrylate copolymer. In another embodiment, the solidifying agent includes polyvinyl alcohol or a polyvinyl alcohol copolymer such as polyvinyl alcohol-polyethylene glycol copolymer.

Preferred solidifying agents are selected from hydroxy propyl cellulose, ammonia methacrylate and acrylates/octylacrylamide copolymer.

For most compositions, the weight percentage of the solidifying agent(s) can be from about 5 wt % to about 60 wt %, and more preferably from about 5 wt % to about 40 wt %, based on the total weight of the composition.

The non-volatile solvent system and the solidifying agent are preferably compatible with one other. Compatibility can be defined as i) the solidifying agent does not substantially negatively influence the function of the non-volatile solvent system; ii) the solidifying agent can hold the non-volatile solvent system in the solidified layer so that substantially no non-volatile solvent oozes out of the layer, and iii) the solidified layer formed with the selected non-volatile solvent system and the solidifying agent has acceptable flexibility, rigidity, tensile strength, elasticity, and adhesiveness. The weight ratio of the non-volatile solvent system to the solidifying agent can be from about 0.01:1 to about 100:1, or more preferably from about 0.05:1 to about 40:1. In some embodiments, the non-volatile solvent system makes up about 20-60% of the total weight of the formulation.

The thickness of the topical pharmaceutical composition layer applied on the skin should also be appropriate for a given formulation and desired antibiotic delivery considerations. If the layer is too thin, the amount of the antibiotic may not be sufficient to support sustained delivery over the desired length of time. If the layer is too thick, it may take too long to form a non-messy outer surface of the solidified layer. If the antibiotic is very potent and the solidified layer has very high tensile strength, a layer as thin as 0.01 mm may be sufficient. If the antibiotic has rather low potency and the solidified layer has low tensile strength, a layer as thick as 2-3 mm may be desirable. Thus, for most antibiotics and compositions, the appropriate thickness can be from about 0.01 mm to about 3 mm, 0.1 mm to about 2 mm, or from about 0.2 mm to about 0.4 mm. In one embodiment, the compositions of the present invention can have sufficient gas volatile solvents such that the formulation can be contained in a pressurized container and applied to the skin by spraying.

In a further embodiment the compositions may also include various agents and ingredients commonly employed in dermatological or cosmetic compositions such as perfumes, coloring agents and antioxidants.

Preferred compositions are:

| Substance | Amount | Source |
|---|---|---|
| Azithromycine | 1-7 g | Chemos GmbH |
| Hydroxypropylcellulose (Type MF EP) | 0.5-1 g | — |
| MIGLYOL 812 (medium chain triglycerides) | 1-2 g | Hüls AG |
| Octylacrylamide Copolymer (DERMACRYL 79) | 1-2 g | National Starch CAS 129702-02-9 |
| Ethanol 94% | ad 30 g | — |

In view of the findings that the spirochetal form of *Borrelia burgdorferi* is the prevailing form at the early infection stage and said form has a high metabolic activity, it is preferred to apply the topical pharmaceutical composition as short as possible, preferably less than one day and more preferably less than two days, after the tick bite. However, the instant topical pharmaceutical compositions allow for a very good penetration of the antibiotic into intracellular and interstitial tissue compartments eradicating also the cystic and spherical forms of *Borrelia burgdorferi* and thus offer a high rate of successful prevention even if applied up to 7 days, preferably up to 5 days, after the tick bite. These findings may be translated in a dosage regimen whereby the topical pharmaceutical composition is applied to the site of the tick bite up to 7 days after the tick bite at least once a day for a period of at least 4 days. Preferred are dosage regimens whereby the topical pharmaceutical composition is applied to the site of the tick bite up to 5 days after the tick bite. Further preferred are dosage regimens whereby the topical pharmaceutical composition is applied to the site of the tick bite at least twice a day.

Further preferred are dosage regimens whereby the topical pharmaceutical composition is applied to the site of the tick bite for a period of at least 3 days.

Concentrations, amounts, and other numerical data may be expressed or presented herein in a range format. It is to be understood that such a range format is used merely for convenience and brevity and thus should be interpreted flexibly to include not only the numerical values explicitly recited as the limits of the range, but also to include all the individual numerical values or sub-ranges encompassed within that range as if each numerical value and sub-range is explicitly recited. As an illustration, a numerical range of "about 0.01 to 2.0 mm" should be interpreted to include not only the explicitly recited values of about 0.01 mm to about 2.0 mm, but also include individual values and sub-ranges within the indicated range.

EXAMPLES

The following examples illustrate the embodiments of the invention that are presently best known. However, it is to be understood that the following are only exemplary or illustrative of the application of the principles of the present invention. Numerous modifications and alternative compositions, methods, and systems may be devised by those skilled in the art without departing from the spirit and scope of the present invention. The appended claims are intended to cover such modifications and arrangements. Thus, while the present invention has been described above with particularity, the following examples provide further detail in connection with what are presently deemed to be the most practical and preferred embodiments of the invention.

Composition A

| Component | Composition [mg] per unit [1 g] | Function |
| --- | --- | --- |
| Erythromycin base | 150 | antibiotic |
| Isopropyl myristate | 40 | non-volatile solvent |
| Glycerol triacetate | 40 | non-volatile solvent |
| Butylhydroxytoluene | 0.4 | antioxidant |
| Ammonia methacrylat, pure | 300 | solidifying agent |
| Water purified | 75 | volatile solvent |
| Ethanol 94% | ad 1 g | volatile solvent |

Composition B

| Component | Composition [mg] per unit [1 g] |
| --- | --- |
| Erythromycin base | 150 |
| DERMACRYL 79 (acrylate/acrylamide copolymer) | 50 |
| KLUCEL MF (hydroxypropyl cellulose) | 25 |
| MIGLYOL 812 (medium chain triglycerides) | 50 |
| Ethanol 94% (w/w) | ad 1 g |

Composition C

| Component | Composition [mg] per unit [1 g] |
| --- | --- |
| Azithromycin | 150 |
| DERMACRYL 79 (acrylate/acrylamide copolymer) | 50 |
| KLUCEL MF (hydroxypropyl cellulose) | 25 |
| MIGLYOL 812 (medium chain triglycerides) | 50 |
| Ethanol 94% (w/w) | ad 1 g |

One possibility to demonstrate the successful prevention of Lyme disease by topical application of an antibiotic is described in the following animal model.

Spirochetes:

Low-passage (passage 4) *B. burgdorferi* sensu stricto N40 organisms that are infective for mice (Barthold, S. W. et al., Lyme borreliosis in selected strains and ages of laboratory mice, J. Inf. Dis., 1990, 162, p. 133-138) are used in this study. Spirochetes are cultured in modified Barbour-Stoenner-Kelly (BSK II) medium containing Kanamycin (0.8 JII/ml, Sigma, Steinheim, Germany) and Rifampicin (50 µg/ml, Sigma) at 33° C.

Mice:

C3H1HeN (C3H) mice are bred and maintained in individually ventilated caging units (Ehret, Berlin, Germany). C57BU6 RAG1-f-(RAG rf) mice are purchased from the Bundesinstitut für Risikobewertung (Berlin, Germany). Mice are kept under specific pathogen-free conditions in the animal facility at the Institute of Immunology, College of Veterinary Medicine, University of Leipzig, and in accordance with the guidelines approved by the Animal Care and Usage Committee of the Regierungs-präsidium Leipzig, Germany.

Host-Adapted *B. burgdorferi* s.s:

Forty pathogen-free RAGrl-mice are infected by intradermal injection into the shaven backs with $10^6$ *B. burgdorferi* s.s. organisms. Mice are sacrificed by $CO_2$ asphyxiation 7 days post inoculation and heart blood is collected aseptically and pooled. EDTA (0.16%) is added as anticoagulant.

Intradermal Injection of *B. burgdorferi* s.s. into Mice:

Two groups of C3H mice are each inoculated intradermally into the shaven back with 100 µl of the pooled blood from RAG-f-mice containing host-adapted *B. burgdorferi* (the inocula of 100 µl is divided in two adjoining injections).

Application of antibiotic: At days 1, 2 and 3 after the injection, the antibiotic formulated as shown for Composition A or B, respectively, is applied at the injection area.

At day 56 post inoculation mice are sacrificed for subsequent analysis.

Detection of *B. burgdorferi* s.s. in Tissue Samples by Culture:

Aseptically collected tissue samples from the heart, urinary bladder, tarsus and ear are squashed in 200 µl BSK II medium. Tissue homogenates are transferred into 12-ml screw cap tubes containing 6 ml BSK II medium. Cultures are incubated at 33° C. for 6 weeks and examined weekly for spirochetes by dark-field microscopy.

ELISA and Western Blots:

Serum samples of mice collected during necropsy are tested for *B. burgdorferi*-specific antibodies. A computerized kinetic ELISA (KELA) and immunoblot analyses are performed as described by Appel, M. J. G. et al., Experimental Lyme disease in dogs produces arthritis and persistent infection, J. Inf. Dis., 1993, 167, p. 651-664. Sonicated whole *B. burgdorferi* N40 lysate is used as antigen in both tests. Murine *B. burgdorferi*-specific antibodies are detected with goat-anti-mouse immunoglobulin G conjugated to horseradish peroxidase (R&D Systems, Minneapolis, USA). The $C_6$ antigen-specific ELISA is performed with the Quantitative Lyme $C_6$ Antibody Test Kit (IDEXX GmbH, Ludwigsburg, Germany).

Results:

Samples taken from the group of mice having been treated with the topical antibiotic composition A or B, respectively, show a significant reduction in infection of Lyme disease compared to the control group.

In a variation of above described study and instead of transdermal injection of *B. burgdorferi* s.s. into mice, the infection can be done by *B. burgdorferi* s.s infected ticks. *B. burgdorferi* carrying ticks are typically allowed to feed from mice for 5 days before the ticks are removed and the site of feeding is treated with Formulation C. Typically 75 mg formulation C is applied to the site of tick-feed covering a skin diameter of 1.5 cm in diameter, corresponding to approx. 15 mg Azithromycine per day and mouse. Treatment is initiated right after removal of the tick and continues the following 2 days (24 hour interval between each treatment) for a total of 3 treatments.

Results:

There is no infection of Lyme disease detectable when composition C is applied to the area where the ticks were allowed to feed. The topical application of Formulation C results in antibody titers, which are not different from naïve mice (KELA values between 10 and 40), whereas the infected mice show KELA values of 160 to 400.

Especially, the tissue and serum samples taken from different parts of the mice 56 days after the tick bite show no *Borrelia burgdorferi* organisms when cultivated and no specific antigenes are detectable. Tissue probes are taken from heart tissue, bladder, joint and ear. The group of mice topically treated with Formulation C show complete absence of *B. burgdorferi*, whereas *B. burgdorferi* is detected in untreated mice, which are exposed to tick-feed.

The recultivation conditions of *B. burgdorferi* are suitable to detect *B. burgdorferi* in any morphological form known to date. Surprisingly, Formulation C was able to eradicate *B. burgdorferi* in a way, that no infectious agents of *B. burgdorferi* are detected in the target tissues of *B. burgdorferi*.

The invention claimed is:

1. A method for preventing Lyme disease or for the elimination of spirochetal, cystic and/or spherical forms of *Borrelia burgdorferi* resulting from a tick bite on a patient, comprising administering to the site of the tick bite a therapeutically effective amount of a topical pharmaceutical composition comprising azithromycin, a solvent with greater volatility than water, a solvent less volatile than water, and a solidifying agent.

\* \* \* \* \*